US007704074B2

(12) United States Patent
Jensen

(10) Patent No.: US 7,704,074 B2
(45) Date of Patent: Apr. 27, 2010

(54) TWO PIECE DENTAL ANATOMICAL FORM AND HOLDER

(75) Inventor: Steven D Jensen, South Jordan, UT (US)

(73) Assignee: CAO Group, Inc, West Jordan, UT (US)

( * ) Notice: Subject to any disclaimer, the term of this patent is extended or adjusted under 35 U.S.C. 154(b) by 0 days.

(21) Appl. No.: 11/420,536

(22) Filed: May 26, 2006

(65) Prior Publication Data

US 2007/0048687 A1 Mar. 1, 2007

Related U.S. Application Data

(60) Provisional application No. 60/711,328, filed on Aug. 25, 2005.

(51) Int. Cl.
*A61C 9/00* (2006.01)

(52) U.S. Cl. ........................................ 433/37

(58) Field of Classification Search .................. 433/37, 433/38–39, 41–48, 214, 71
See application file for complete search history.

(56) References Cited

U.S. PATENT DOCUMENTS 4,085,507 A * 4/1978 Lehn et al. .................... 433/37
4,227,877 A * 10/1980 Tureaud et al. ............... 433/37
4,459,107 A * 7/1984 Weissman .................... 433/36
4,776,792 A * 10/1988 Wagner et al. ................ 433/71
5,059,120 A * 10/1991 Lee ............................ 433/37
5,127,829 A * 7/1992 Nordquist .................... 433/35
5,460,527 A 10/1995 Kittleston
5,816,802 A 10/1998 Montgomery
5,895,218 A 4/1999 Quinn et al.
6,071,121 A * 6/2000 Simon ......................... 433/37
6,103,800 A 8/2000 Peterson et al.
6,142,780 A 11/2000 Burgio
6,183,251 B1 2/2001 Fischer
6,247,930 B1 6/2001 Chiang et al.
D456,515 S 4/2002 Dinu
6,386,869 B1 5/2002 Zegarelli
6,638,496 B2 10/2003 McLaughlin
6,641,393 B2 11/2003 Trichas
6,749,428 B2 6/2004 DiMarino et al.
6,758,671 B2 7/2004 Brattesani
6,780,401 B2 8/2004 Kim et al.
6,848,905 B2 2/2005 Jacobs et al.
6,860,736 B2 3/2005 Allred et al.
2005/0106529 A1* 5/2005 Abolfathi et al. .............. 433/41

* cited by examiner

*Primary Examiner*—John J Wilson
(74) *Attorney, Agent, or Firm*—Geoffrey E. Dobbin

(57) ABSTRACT

The present invention is a thermally formable plastic anatomical form for dentistry and a holder for the same. The holder is specially adapted to accommodate the plastic form in that it is heat resistant and features a bite guide to assure an even distribution of the plastic around the teeth of the patient and thickened occlusal surfaces to register specific tooth impressions more readily. The form according to the present invention may be used in any conventional dental work where a form may be needed, such as tray creation and stone molds, or may be utilized with therapeutic plastics so as to become a therapeutic dental device in and of itself.

5 Claims, 4 Drawing Sheets

18
22
16
14
20
12

TWO PIECE DENTAL ANATOMICAL FORM AND HOLDER

CROSS REFERENCE TO RELATED APPLICATIONS

This application claims priority as a non-provisional perfection of prior filed provisional application 60/711,328, filed Aug. 25, 2005.

FIELD OF THE INVENTION

The present invention relates to the field of anatomical forms and more particularly relates to an improved structure for obtaining a dental form.

BACKGROUND OF THE INVENTION

Prior art anatomical impressions in dentistry are utilized to make crowns and treatment trays for an individual patient. Typically, a tray is loaded with an alginate or polyvinyl siloxane substance and placed in a patient's mouth until it cures. Then the tray is removed and the impression used to make a cast of the patient's mouth. Until now, patients had to wait for the substance to cure before a true impression was made. The present invention departs from the prior art in that it utilizes a thermally set plastic, which can be imprinted and removed in moments. The present invention is also available for use with therapeutic plastics, thus directly creating a dental device for treatment of a patient.

BRIEF SUMMARY OF THE INVENTION

In view of the foregoing disadvantages inherent in the known methods of obtaining dental impressions, this invention provides an improved anatomical form. As such, the present invention's general purpose is to provide a means to create an anatomical form that surrounds or fits into one or more dental surfaces. To accomplish these objectives, the form and holder according to the present invention comprise a form that is made of a thermally sensitive plastic or plastic combination which is positioned in a holder while softened, imprinted and cooled into the final form. The anatomical form may be made of a therapeutic plastic, thus directly becoming a treatment device for oral hygiene.

The more important features of the invention have thus been outlined in order that the more detailed description that follows may be better understood and in order that the present contribution to the art may better be appreciated. Additional features of the invention will be described hereinafter and will form the subject matter of the claims that follow.

Many objects of this invention will appear from the following description and appended claims, reference being made to the accompanying drawings forming a part of this specification wherein like reference characters designate corresponding parts in the several views.

Before explaining at least one embodiment of the invention in detail, it is to be understood that the invention is not limited in its application to the details of construction and the arrangements of the components set forth in the following description or illustrated in the drawings. The invention is capable of other embodiments and of being practiced and carried out in various ways. Also it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION OF THE INVENTION

Figure 1:
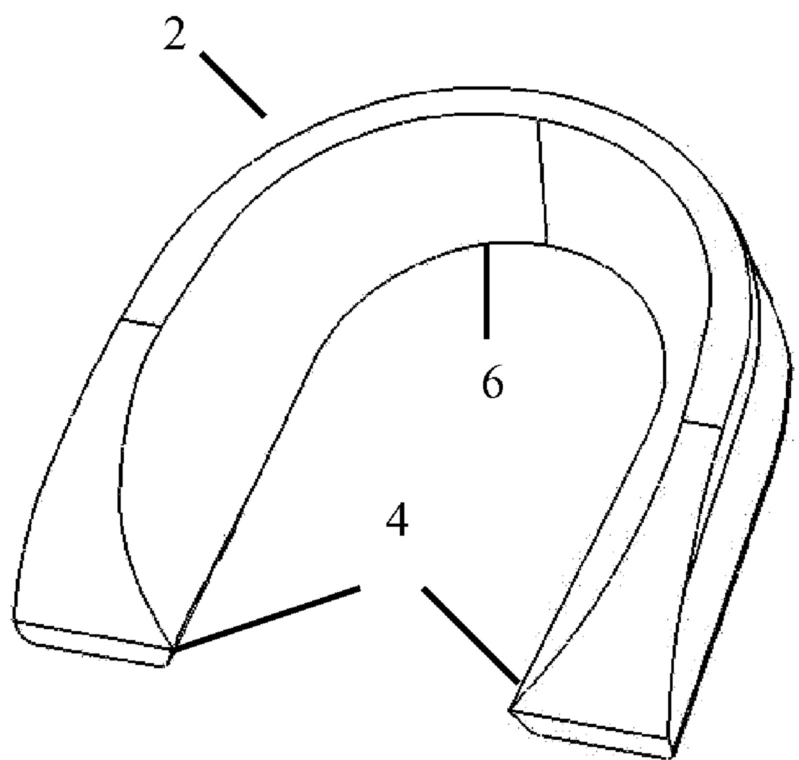
FIG. 1 is a perspective view of the anatomical form.

With reference now to the drawings, the preferred embodiment of the anatomical form and holder is herein described. It should be noted that the articles "a", "an" and "the", as used in this specification, include plural referents unless the content clearly dictates otherwise.

In order to create a custom anatomical form in a softened thermoplastic it must be contained in a pre-designed outer shell that maintains its shape, integrity and not melt. This pre-designed outer shell is one of two pieces and called the "Form Holder", shown in FIGS. 4-7. The form holder's function is to contain the anatomical form while it is in the molten or softened state before and as a bite is registered into the form. Therefore, it is advantageous to design into the form holder as many features that would facilitate the fit, shape and uniformity as possible. The form holder is made from any thermoplastic that has a significantly higher melting point than the anatomical form, usually >100° C. The form holder must remain intact during the process of softening the anatomical form. The form holder may be designed to surround an arch, or a partial arch, of teeth or any dental surface.

The form holder is comprised of three basic parts. The first is an outer wall 16 roughly perpendicular to a floor 14. Protruding inwards at an angle to the floor 14 is an inner wall 20. Together, these surfaces contain the form in its softened state. Ideally, the form holder 12 includes a protruding handle 22 to help the patient move and orient the form during the fitting process. A patient may grasp said handle 22 between the thumb and one or two fingers of the hand to guide the form into the mouth.

When registering a patient's bite into softened plastic it is advantageous to have a uniform layer of plastic on the buccal and lingual surfaces of the anatomical form. Therefore, the form holder 12 is designed with a bite guide 18, an arch shaped ledge that protrudes from the buccal side of the form holder 12. The bite guide 18 directs the placement of the teeth immediately before biting to register ones teeth. The patient simply inserts the form holder 12 until the teeth make contact with the bite guide 18, then the patient can bite knowing that their teeth are orientated in a pre-determined position creating for them a uniform form. Without the bite guide 18, an anatomical form can be made with one wall flimsy and the opposing wall too thick, which makes for a poor fit.

The form holder can be designed with a thickened occlusal surfaces 24 for the molars. Said design leaves a characteristic depression in the region of the incisors and cuspids. The purpose of this depression is to allow the incisors and cuspids to be surrounded with plastic while avoiding contact with the form holder 12. This design allows the cuspids and incisors to have an especially custom fit that mechanically aids in retention on the teeth and allows them to be completely enveloped in plastic. The highest occlusal points of the molars will often be very thin and show through in the anatomical form; since it is those surfaces that make contact with the form holder. This design can be reversed, having a thickened apex 26, with equal effectiveness to emphasize the molars rather than the front teeth.

Figure 2:
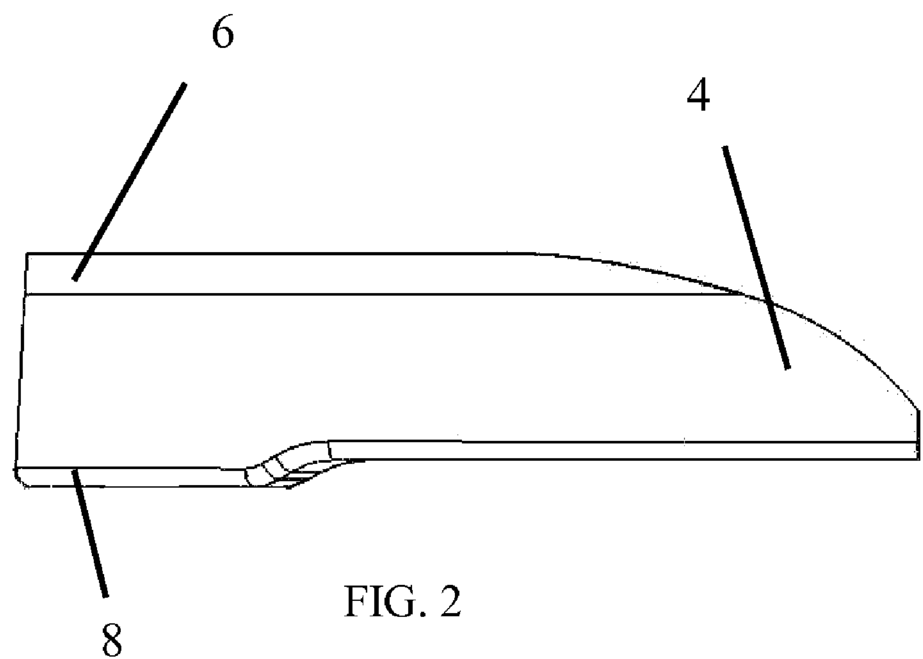
FIG. 2 is a side view of the anatomical form.
Figure 3:
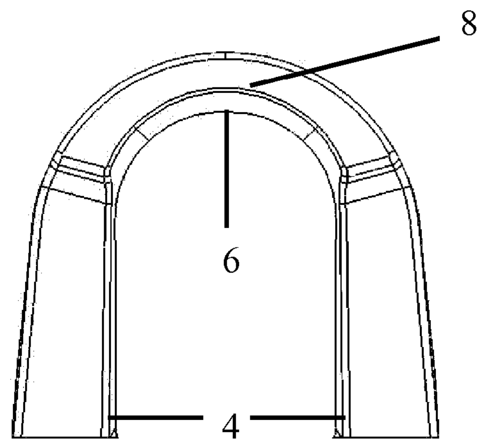
FIG. 3 is a bottom view of the anatomical form.
Figure 4:
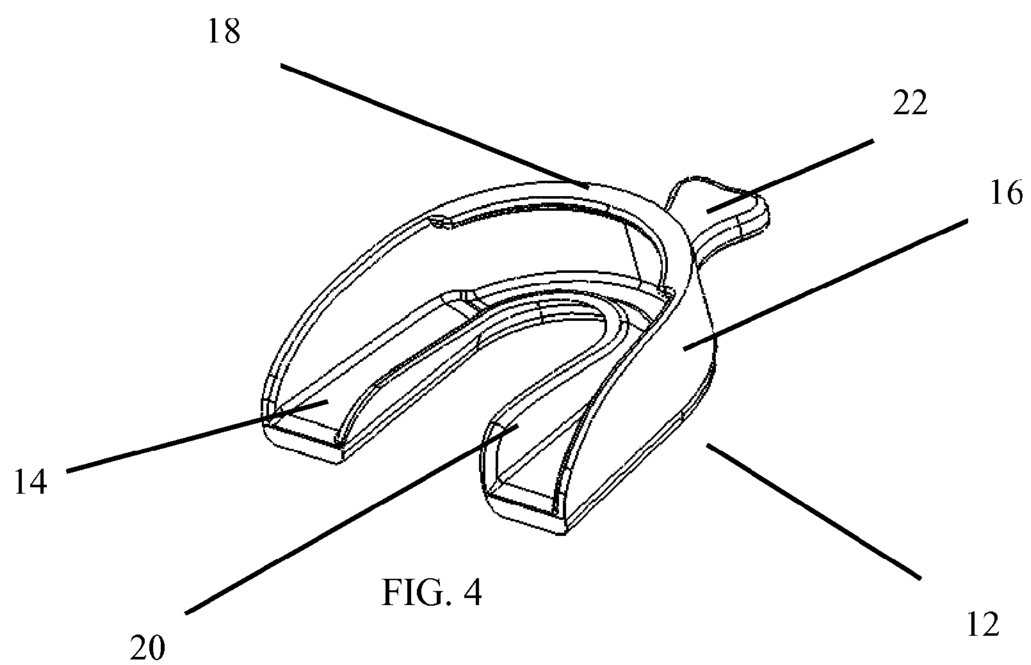
FIG. 4 is a perspective view of the arch form holder.
Figure 5:
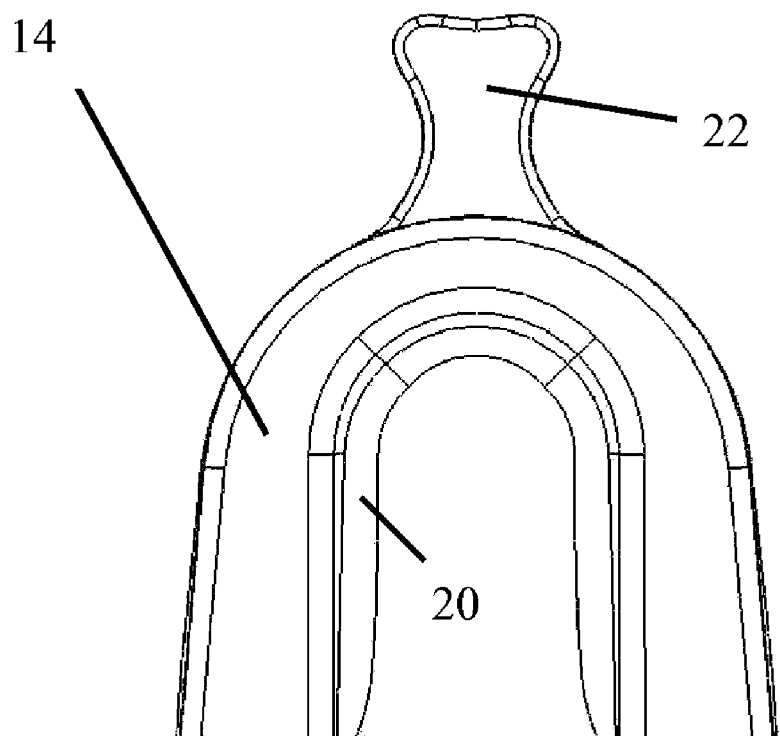
FIG. 5 is a bottom view of the form arch holder.
Figure 6:
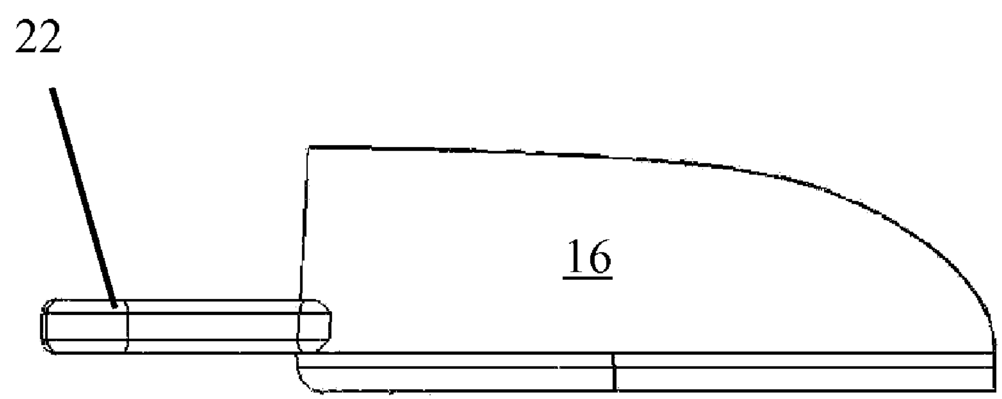
FIG. 6 is a side view of the form arch holder.
Figure 7:
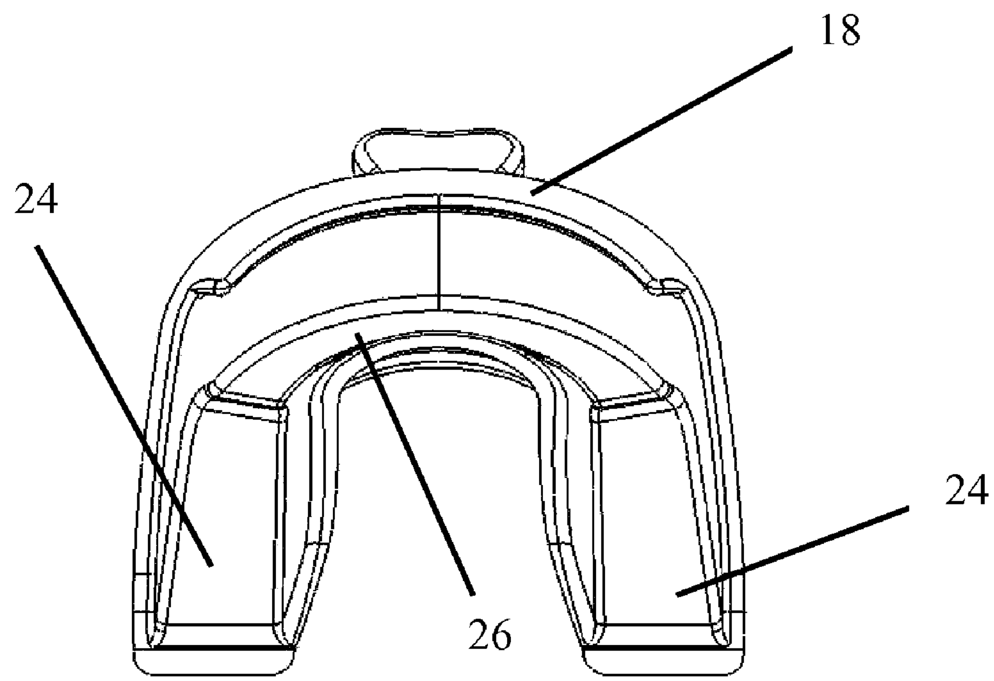
FIG. 7 is an isometric view of the arch form holder.
Figure 8:
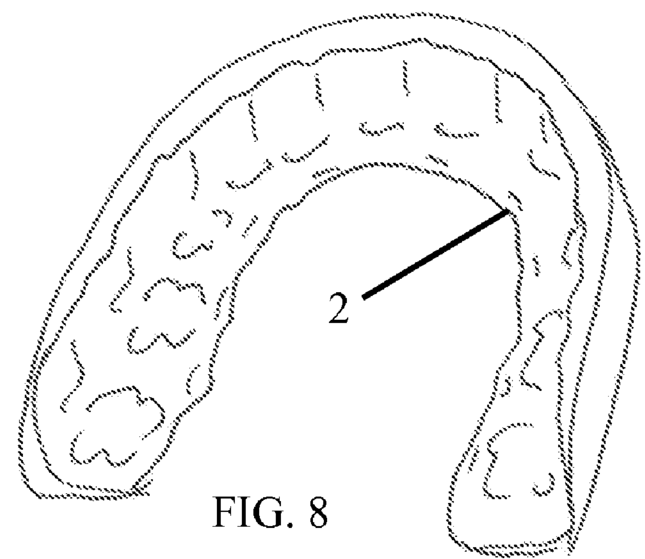
FIG. 8 is a perspective view of the anatomical form after bite registration.

The anatomical form 2, shown in FIGS. 1-3, installs inside the form holder 12. Said anatomical form 2 can be selected from a thermoplastic that can melt or be softened in a range that a patient's mouth can tolerate. The anatomical form, when heated, softens enough so that a bite or arch can be registered into the plastic. Said thermoplastic can then be fixed into place by cooling the plastic until it becomes hardened or solid. The solidified anatomical form can then be peeled away from the form holder, thus leaving the patient with a form fitting anatomical form. Said finished form can be trimmed of excess material to eliminate any annoyance. The above given process can produce a uniform anatomical form with a snug mechanical fit. In the given drawings, the form is basically an arch shape with an apex 6, to register incisors and cuspids, and ends 4 to register molars. To compensate for thickening of the form holder 24, form is thickened 8 at the arch 6. FIG. 8 depicts the form 2 after registration of a bite.

Although the present invention has been described with reference to preferred embodiments, numerous modifications and variations can be made and still the result will come within the scope of the invention. No limitation with respect to the specific embodiments disclosed herein is intended or should be inferred.

What is claimed is:

1. A dental device comprising:

a. a form holder, further comprising:

i. an interior floor in the shape of at least a partial arch, having both an interior edge and an exterior edge, generally defining a horizontal plane and upon which an anatomical form will directly rest;

ii. a buccal wall shaped in conformity with the floor and extending generally perpendicularly from the external edge;

iii. a lingual wall shaped in conformity with the floor and extending obtusely from the interior edge of said floor; said lingual wall, floor and buccal wall defining a chamber and the volume immediately above the floor being defined as a bite zone; and iv. a bite guide being an arch shaped ledge extending generally perpendicularly from the buccal wall, parallel to the floor and extending into the bite zone; and b. an anatomical form shaped in conformity with the chamber and made of a thermally sensitive plastic having a substantially lower melting point than the material from which the form holder is made, the anatomical form resting directly on the floor;

wherein, the form is installed into the holder and the holder and form are heated to a softening point of the form and then the holder, with the softened form, is placed in a patient's mouth to register a dental imprint which is then removed from the patient's mouth and cooled rapidly to create a form fitting mold of the patient's dental features.

2. The dental device of claim 1, the form holder further comprising an exterior handle, protruding from the exterior wall.

3. The dental device of claim 1, the floor having at least one thickened occusal surface.

4. The dental device of claim 3, the at least one thickened occulsal surface being at the apex of and arch defined by the holder.

5. The dental device of claim 3, the at least one thickened occulsal surface being at the bases of an arch defined by the holder.

* * * * *